United States Patent
Piot et al.

(10) Patent No.: US 6,375,941 B1
(45) Date of Patent: Apr. 23, 2002

(54) MASCARA PRODUCT COMPRISING A POLYURETHANE

(75) Inventors: Bertrand Piot, Paris; Valérie de la Poterie, Le Chatelet en Brie; Fréderic Auguste, Chevilly-Larue; Sophie Bodelin, Vanves, all of (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/460,393

(22) Filed: Dec. 13, 1999

(30) Foreign Application Priority Data

Dec. 14, 1998 (FR) ............................................. 98 15762

(51) Int. Cl.[7] ............................................. A61K 7/06
(52) U.S. Cl. .................. 424/70.7; 424/70.1; 424/70.11; 424/70.12; 424/70.15; 424/70.16
(58) Field of Search ............................. 424/70.1, 70.7, 424/70.11, 70.12, 70.15, 70.16

(56) References Cited

U.S. PATENT DOCUMENTS

| | | | |
|---|---|---|---|
| 4,988,502 A | * | 1/1991 | Ounanian et al. |
| 5,053,221 A | * | 10/1991 | Robertson et al. |
| 5,490,737 A | | 2/1996 | Gueret |
| 5,643,581 A | | 7/1997 | Mougin et al. |
| 5,650,159 A | | 7/1997 | Lion et al. |
| 5,794,632 A | | 8/1998 | Gueret |
| 5,843,417 A | * | 12/1998 | Hanna et al. ............... 424/70.7 |
| 5,849,278 A | | 12/1998 | Piot et al. |
| 5,866,111 A | * | 2/1999 | Felardos et al. |
| 5,911,973 A | | 6/1999 | de la Poterie |
| 5,972,354 A | * | 10/1999 | de la Poterie et al. |
| 6,106,813 A | * | 8/2000 | Modet et al. |
| 6,166,093 A | | 12/2000 | Mougin et al. |
| 6,197,316 B1 | * | 3/2001 | Ellingson et al. ............. 424/401 |
| 6,214,329 B1 | * | 4/2001 | Brieva et al. ............... 424/70.7 |

FOREIGN PATENT DOCUMENTS

| | | |
|---|---|---|
| EP | 0 611 170 | 8/1994 |
| EP | 0 627 182 | 12/1994 |
| EP | 0 637 600 | 2/1995 |

(List continued on next page.)

OTHER PUBLICATIONS

English–language Abstract of JP 5 339130.
English–language Abstract of FR 2 743 297A1.
English language abstract of EP 0 611 170.
English language translation of EP 0 637 600.
English language Derwent Abstract of EP 0 655 234.
English language abstract of EP 0 751 162.
English language abstract of EP 0 811 336.
English language abstract of EP 0 811 337.
English language abstract of EP 0 842 620.
English language abstract of FR 2 528 699.
English language Derwent Abstract of FR 2 607 373.
English language Derwent Abstract of FR 2 705 876.

* cited by examiner

*Primary Examiner*—Diana Dudash
*Assistant Examiner*—Gina Yu
(74) *Attorney, Agent, or Firm*—Finnegan, Henderson, Farabow, Garrett & Dunner, L.L.P.

(57) ABSTRACT

The invention relates to a application system for coating, in particular, for making up, keratin fibers, having a reservoir containing a composition for coating, in particular, for making up keratin fibers, in particular, the eyelashes, a removable closure means designed to close the reservoir and an applicator member for applying the composition to the fibers, wherein the coating composition has an aqueous medium and a film-forming polyurethane in the form of solid particles dispersed in the aqueous medium, the composition having a viscosity, measured at 25° C., at a shear rate of 200 $s^{-1}$, ranging from 5 Pa·s to 18 Pa·s, and wherein the composition is free of wax.

35 Claims, 1 Drawing Sheet

FOREIGN PATENT DOCUMENTS

Figure 1:
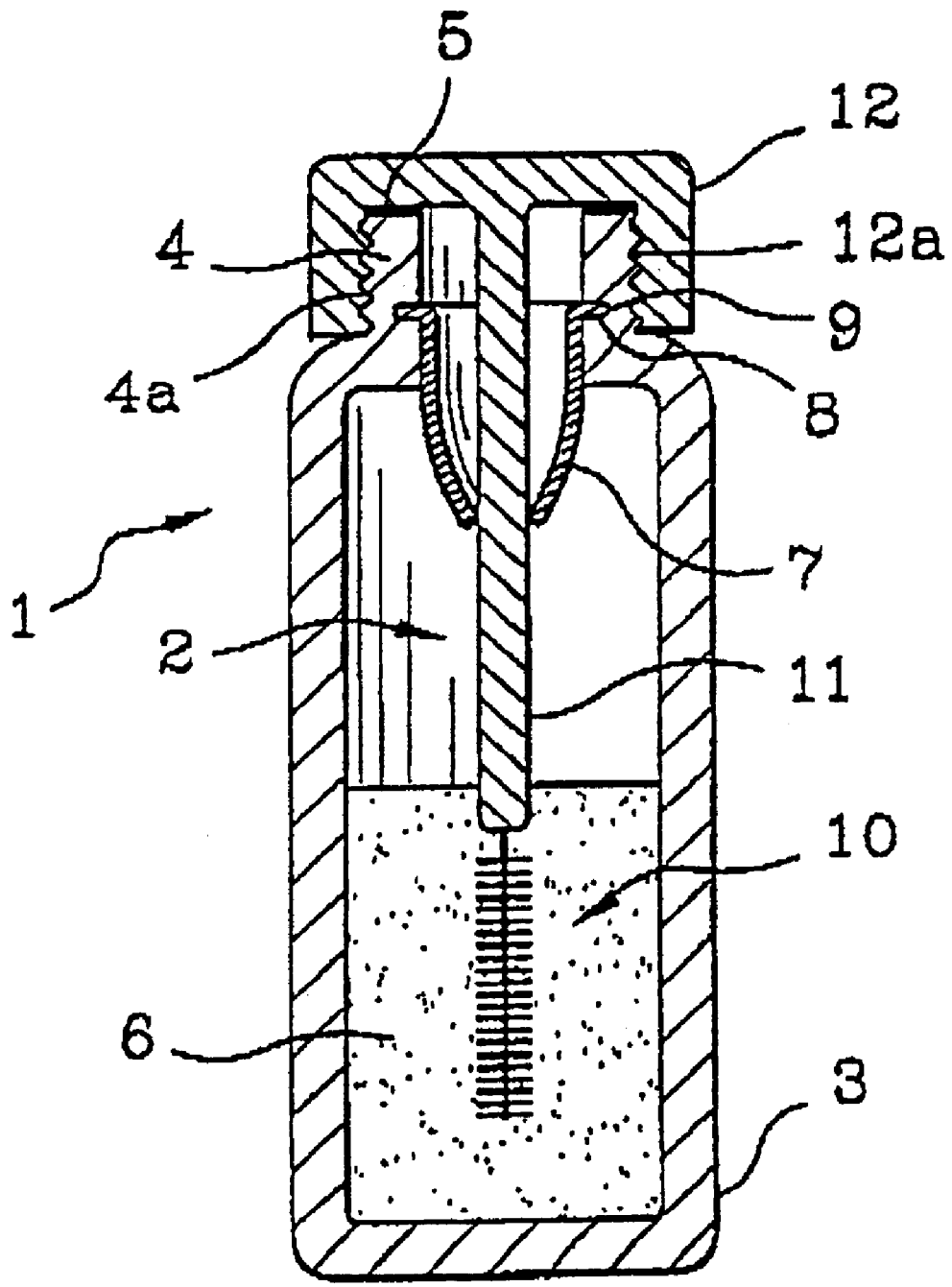

| | | |
|---|---|---|
| EP | 0 655 234 | 5/1995 |
| EP | 0 751 162 | 1/1997 |
| EP | 0 811 336 | 12/1997 |
| EP | 0 811 337 | 12/1997 |
| EP | 0 842 620 | 5/1998 |
| EP | 0 856 306 A2 | 8/1998 |
| EP | 0 856 306 | 8/1998 |
| EP | 0 856 307 A2 | 8/1998 |
| FR | 2 528 699 | 12/1983 |
| FR | 2 607 373 | 6/1988 |
| FR | 2 687 569 A1 | 8/1993 |
| FR | 2 705 876 | 12/1994 |
| FR | 2 705 876 A1 | 12/1994 |
| FR | 2 708 199 A1 | 2/1995 |
| FR | 2 721 034 A1 | 12/1995 |
| FR | 2 733 398 A1 | 10/1996 |
| FR | 2 736 057 A1 | 1/1997 |
| FR | 2 743 297 A1 | 7/1997 |
| JP | 5 339130 | 12/1993 |
| JP | 6 9341 | 1/1994 |
| JP | 7 51122 | 2/1995 |
| JP | 7 89822 | 4/1995 |
| JP | 7 330539 | 12/1995 |
| JP | 8 317816 | 12/1996 |
| JP | 9 12425 | 1/1997 |
| JP | 10 509742 | 9/1998 |
| JP | 10 306014 | 11/1998 |

MASCARA PRODUCT COMPRISING A POLYURETHANE

The present invention relates to a product for coating, in particular, for making up, keratin fibers, in particular, human eyelashes and hair, comprising a polyurethane. The invention also relates to a process for coating, in particular, for making up, keratin fibers. The make-up product and process, according to the invention are more particularly intended for essentially longilinear keratin fibers such as the eyelashes, the eyebrows and the hair, including false eyelashes and wigs. The product of the invention can be a make-up product, a make-up base, a composition to be applied on or over make-up, named a topcoat, or a cosmetic treatment product for keratin fibers. The invention relates more particularly to a mascara.

Mascaras are commonly prepared as wax-based formulations according to two types: aqueous mascaras, known as cream mascaras, in the form of an emulsion of waxes in water; and anhydrous mascaras or mascaras with a low water content, known as waterproof mascaras, in the form of dispersions of waxes in solvents.

However, the film of make-up obtained with the inventive composition applied to eyelashes has a tendency to crumble over time; grains become deposited and leave marks around the eyes. Furthermore, the film thus embrittled is not resistant to rubbing, in particular, by the fingers, and/or to water, for example, when bathing or taking a shower. The make-up is thus not resistant and has poor staying power over time.

It is known to use, with the waxes, film-forming polymers which can be dissolved or dispersed in an aqueous medium, as described, in particular, in French Patent Application No. FR-A-2,528,699 and European Patent Application No. EP-A-655,234. However, the presence of waxes leads to poor staying power of the make-up over time, especially with respect to water and rubbing.

An object of the present invention,is thus to provide a mascara composition leading to a make-up effect that has good staying power over time.

The inventors have obtained such a mascara with a composition free of wax and comprising a film-forming polyurethane. The composition, which is easy to apply, coats the eyelashes well. The make-up effect is natural, comfortable and has good staying power over time; the film does not crumble after a day and is easy to remove with water, in particular, warm water.

More specifically, a subject of the invention is a system or product for coating, in particular, for making up, keratin fibers, comprising a reservoir containing a composition for coating, in particular, for making up, keratin fibers, especially the eyelashes, an applicator member and a removable closure means designed to close the reservoir, wherein the coating composition comprises an aqueous medium and a film-forming polyurethane in the form of solid particles dispersed in the aqueous medium, the composition having a viscosity, measured at 25° C., at a shear rate of 200 s$^{-1}$, ranging from 5 Pa·s (50 poises) to 18 Pa·s (180 poises), the composition furthermore being free of wax.

Another subject of the invention is a process for coating, in particular, for making up, keratin fibers, especially the eyelashes, wherein a coating composition, in particular, a make-up composition of the system defined above is applied along the length of the keratin fibers.

Another subject of the invention is the use of a coating composition, in particular, a make-up composition, as defined above, to obtain a coating, in particular, a make-up effect which has good staying power and/or which can be removed with water.

Additional features and advantages of the invention are set forth in the description that follows, and, in part, will be apparent from the description or may be learned from practice of the invention. The advantages of the invention will be realized and attained by the compositions, systems, and processes particularly pointed out in the written description and claims.

Both the foregoing general description and the following detailed description of the invention are exemplary and explanatory only and are not restrictive of the claimed invention.

In the present patent application, the expression "wax-free composition" means a composition that does not contain any compound solid at room temperature (25° C.), and that has a melting point ranging from 45° C. to 110° C.

The polyurethane used according to the invention can advantageously be chosen from polyester-polyurethanes, acrylic-polyurethanes, polyether-polyurethanes, and siliconed-polyurethanes. The polyurethane can preferably be an anionic polyurethane.

According to a first embodiment of the invention, the polyurethane can have a water uptake of less than or equal to 30%, and, in particular, ranging from 0.5% to 15%. The polyester-polyurethanes according to the invention have such water uptake properties. Such polyurethanes make it possible to obtain a make-up product having good staying power over time, in particular, for more than one day, or even two to three days, and good water-resistance. Advantageously, polyurethanes, and, in particular, polyester-polyurethanes, capable of forming a film having a hardness ranging from 40 to 200 seconds, and, better still, from 50 to 170 seconds, can be used.

According to the present application, the expression "water uptake of the polyurethane" means the percentage of water absorbed by the polyurethane after immersion in water at 30° C. for 10 minutes. The water uptake is measured for a layer 300 µm thick (before drying) deposited on a plate and then dried for 24 hours at 30° C. and at 50% relative humidity; pieces of about 1 cm$^2$ cut from the dry film are weighed (mass measurement M1) and then immersed in water for 10 minutes. After immersion, the piece of film is dried to remove the excess surface water and then weighed (mass measurement M2). The difference M2–M1 corresponds to the amount of water absorbed by the polymer. The water uptake is equal to (M2–M1)/M1×100, and is expressed as a percentage by weight of water relative to the weight of polymer.

The hardness of the polymer film is measured on a film obtained after drying, for 24 hours at 30° C. and at 50% relative humidity, of a layer 300 µm thick (before drying) of an aqueous dispersion containing 28% solids of the particles of radical-generated polymer. The hardness of the film is measured according to ASTM standard D-43-66, or standard NF-T 30-016 (October 1981), using a Persoz pendulum.

According to a second embodiment of the invention, the polyurethane can have a water uptake of greater than 30%, preferably from 30% to 150% and, better still, from 40% to 100%. The polyether-polyurethanes according to the invention have such water uptake properties. Such polyurethanes make it possible to obtain a make-up product which adheres well to the eyelashes, having good staying power over time and being easy to remove with water, in particular warm water at 35–45° C. Advantageously, polyurethanes and, in particular, polyether-polyurethanes, capable of forming a film having a hardness ranging from 10 to 40 seconds, and, better still, from 20 to 35 seconds, can be used.

The polyurethane particles dispersed in the aqueous medium of the composition generally have a size preferably ranging from 10 nm to 200 nm.

Polyester-polyurethanes that can be used are those sold under the names "Avalure UR-425", "Avalure UR-430", "Avalure UR-405" and "Avalure UR-410" by the company Goodrich, and "NEOREZ R-989" by the company Zeneca.

Polyether-polyurethanes that can be used are those sold under the names "Sancure 878", "Avalure UR-450" and "Sancure 861" by the company Goodrich.

The term "acrylic-polyurethanes" means polyurethanes comprising at least one acrylic polymeric chain, or polyurethane/acrylic hybride polymers. Acrylic polyurethanes that can be used are those sold under the names "UCECOAT DW 5560," "UCECOAT DW 5561," "UCECOAT DW 5160," "UCECOAT DW 5460," and "UCECOAT DW 5660" by the company UCB, "FLEXTHANE 610," "FLEXTHANE 620," and "FLEXTHANE 630" by the company Air Products, and "SANCURE AU-4000" and "SANCURE XPD-2361" by the company Goodrich.

The polyurethane is present in the composition of the product according to the invention in an amount effective to form a film on the keratin fibers. The polyurethane can be present in the composition of the product according to the invention in a content, by weight of solids, ranging from 5% to 60% by weight relative to the total weight of the composition, preferably from 10% to 45% by weight, and, better still, from 15% to 35% by weight.

The aqueous medium of the composition can comprise water. It can also comprise a mixture of water and water-miscible solvent, such as lower monoalcohols containing from 1 to 5 carbon atoms, $C_3$–$C_4$ ketones or $C_3$–$C_4$ aldehydes. The water-miscible solvent is preferably ethanol. The content of water-miscible solvent can range from 0.1% to 15% by weight, and, better still, from 1% to 8% by weight, relative to the total weight of the composition.

Advantageously, the composition can have a viscosity ranging from 6 Pa·s (60 poises) to 15 Pa·s (150 poises), and, better still, from 7 Pa·s (70 poises) to 12 Pa·s (120 poises). Such a viscosity allows fast and easy application of the composition, as well as uniform coating over the entire length of the eyelashes. The viscosity is measured at 25° C. with a Rheomat RM 180 viscometer fitted with a No. 4 rotor, the measurement being carried out after spinning the rotor for 10 minutes (after which time stabilization of the viscosity and of the rotor spin speed are observed), at a shear rate of 200 $s^{-1}$.

To give the composition according to the invention the viscosity required for application to keratin fibers, and, in particular, the eyelashes, the composition can comprise a thickener for adjusting the desired viscosity.

Examples of thickeners that can be used according to the invention, include:

cellulose-based thickeners, for example, water-soluble cellulose-based thickeners, such as hydroxyethylcellulose, methylcellulose, hydroxypropylcellulose and carboxymethylcellulose. Among these thickeners, preferred examples include the gums sold under the name "Cellosize QP 4400 H" by the company Amerchol, guar gum, in particular, those sold under the name Vidogum GH 175 by the company Unipectine and under the name Jaguar C by the company Meyhall, the quaternized guar gum sold under the name "Jaguar C-13-S" by the company Meyhall, nonionic guar gums comprising $C_1$–$C_6$ hydroxyalkyl groups. Mention may be made, for example, of hydroxymethyl, hydroxyethyl, hydroxypropyl and hydroxybutyl groups. Such guar gums are sold, in particular, under the trade names Jaguar HP8, Jaguar HP60, Jaguar HP120 and Jaguar HP 105 by the company Meyhall, or under the name Galactasol 40H4FD2 by the company Aqualon, xanthan gum, carob gum, scleroglucan gum, gellan gum, rhamsan gum and karaya gum, alginates, maltodextrin, starch and its derivatives, hyaluronic acid and its salts, clays, and, in particular, montmorillonites, hectorites and laponites, crosslinked polyacrylic acids, such as the "Carbopol" products from the company Goodrich, the polyglyceryl (meth)acrylate polymers sold under the names "Hispagel" or "Lubragel" by the companies Hispano Quimica or Guardian, polyvinylpyrrolidone, polyvinyl alcohol, crosslinked acrylamide polymers and copolymers, such as those sold under the names "PAS 5161" or "Bozepol C" by the company Hoechst, "Sepigel 305" by the company SEPPIC, crosslinked methacryloyloxyethyltrimethylammonium chloride homopolymers sold under the name "Salcare SC95" by the company Allied Colloid, and associative polymers and, in particular, associative polyurethanes.

In the composition according to the invention, the thickener can be present in an effective amount for the composition to have the viscosity as defined above. The thickener content can range, for example, from 0.1% to 10% by weight relative to the total weight of the composition, and preferably from 0.5% to 5% by weight.

The composition can also comprise other ingredients usually used in cosmetics. Such ingredients can be chosen, in particular, from plasticizers, coalescence agents, fillers, dyestuffs, such as pigments or dyes, surfactants, preserving agents, oils, cosmetic agents, such as moisturizers and anti-UV agents that are well known in the prior art. Needless to say, a person skilled in the art will take care to select this or these optional additives and/or the amount thereof, such that the advantageous properties of the make-up product are conserved.

Fillers that can be used, in particular, are the fillers usually used in mascara compositions. It is possible, for example, to use fumed silica, in particular, to obtain a thicker make-up effect on the eyelashes. Fillers particularly preferred for the composition according to the invention are, in particular, starch, such as rice starch, talc and polytetrafluoroethylene; these fillers are highly compatible with the aqueous medium of the composition and are easy to incorporate into the composition. In addition, they allow a smooth, shiny film of make-up to be obtained.

The fillers can be present in the composition in a content ranging from 0.1% to 6% by weight relative to the total weight of the composition.

The composition can also comprise an auxiliary film-forming polymer, to allow the cosmetic and physicochemical properties of the film of make-up to be modified. This auxiliary film-forming polymer can be in dissolved form or in the form of solid particles dispersed in the aqueous medium of the composition.

Examples of auxiliary film-forming polymers include vinyl polymers and, in particular, acrylic polymers, or, alternatively, polyesters, such as polyesters containing a sulphonic group.

The coating composition, in particular, the make-up composition, could be packaged in an application system comprising a reservoir containing the composition. The system could include a number of additional components. For example, the system could include a removable closure for closing the reservoir, preferably in a leaktight manner. The application system could also comprise an applicator member configured to apply the make-up composition to the keratin fibers, and, in particular, to the eyelashes. The applicator member is preferably configured to be loaded with the composition and then used to deposit the composition on the eyelashes. In a preferred embodiment, the applicator member is integral with the closure of the system.

The application system could also comprise a wiper for wiping excess composition from the applicator member. The wiper could be integral with the reservoir and configured to wipe the applicator member upon removal of the applicator member from the reservoir.

The applicator member could be a type of applicator configured to apply a substance to keratin fibers. Preferably, the applicator member could be a mascara brush well known to those skilled in the art. The applicator member preferably comprises bristles arranged radially around a twisted core, such as a metal core. The brush can be of varied shapes and can comprise cutout sections. Mascara brushes are described, for example, in French Patent Application No. FR-A-2,607,373 and European Patent Application Nos. EP-A-611,170, EP-A-811,336, EP-A-811,337 and EP-A-842,620, the disclosures of which are incorporated herein by reference.

In one embodiment, the application system could comprise a reservoir containing a mascara composition as defined above, in combination with an applicator member. The applicator member could comprise an applicating portion provided at one end of a shaft. The other end of the shaft could be integral with a handle component optionally configured to resealably close the reservoir.

The application system could also comprise an annular wiper fixed into a neck of the reservoir. When the applicator member is placed in the reservoir, the shaft of the applicator member preferably passes through the wiper. During removal of the applicator member from the reservoir, the wiper is configured to wipe the shaft and/or the applicating surface. Advantageously, the wiper has at least one finger and is provided with a central passage orifice that can optionally be flocked. Such a device is described, in particular, in French Patent Application No. FR-A-2,705,876, the disclosure of which is incorporated herein by reference.

The invention is illustrated in greater detail in the examples below.

FIG. 1 is a longitudinal cross-sectional view of an embodiment of a mascara application system in accordance with the invention.

With reference to FIG. 1, a mascara application system 1, including an applicator member 2 and a reservoir 3, containing a mascara composition 6 having the composition of Example 1 explained below. The reservoir 3 preferably has a threaded neck 4 and a leak-proof seal 5 on the neck 4. A wiper 7 is preferably positioned in the neck 4. The wiper 7 is held in place by means of a flange 8 which cooperates with a recess 9 in the neck 4. The wiper 7 is made, in a known manner, of a flexible, elastic material.

The applicator member 2 preferably comprises an applicating portion 10 fixed to one end of a shaft 11. Preferably, a handle 12 is integral with another end of the shaft 11 opposite the applicating portion 10. The applicating portion 10 is preferably configured like a mascara brush comprising, in a known manner, bristles distributed radially as a helical strip around a twisted core.

The handle 12 preferably includes threading 12a which cooperates with threading 4a of the neck 4 to form a removable lid for the reservoir 3. Leaktight closure of the reservoir 3 is obtained by screwing the handle 12 onto the neck 4 until the handle 12 contacts the seal 5.

The present invention is further illustrated by the following examples which are designed to teach those of ordinary skill in the art how to practice the invention. The following examples are merely illustrative of the invention and should not be construed as limiting the invention as claimed. Examples of mascara compositions that can be packaged in the application system described above are given below.

EXAMPLE OF COMPOSITIONS

Example 1

A mascara having the composition below was prepared:

| | |
|---|---|
| Aqueous dispersion of polyester-polyurethane containing 49% solids (Avalure UR-425 from Goodrich) | 35.8 g AM |
| Hydroxyethyl cellulose (Cellosize QP 4400 H from Amerchol) | 1.82 g |
| Fumed silica (Aerosil 200 from Degussa) | 1.82 g |
| Ethanol | 5 g |
| Propylene glycol | 4.05 g |
| Citric acid | 0.15 g |
| Pigments | 4 g |
| Preserving agents qs | |
| Water qs | 100 g |

The mascara applied easily to the eyelashes and gave a make-up effect that had good staying power for at least one day, and even 2 to 4 days, that was resistant to rubbing with the fingers and could be removed with water.

The mascara was tested on a panel of 17 women: 12 women (70%) found that the mascara had a staying power on the eyelashes of at least 3 days after application.

Example 2

A mascara having the composition below was prepared:

| | |
|---|---|
| Aqueous dispersion of polyester-polyurethane containing 49% solids (Avalure UR-425 from Goodrich) | 24.5 g AM |
| Hydroxyethyl cellulose (Cellosize QP 4400 H from Amerchol) | 1.9 g |
| Fumed silica (Aerosil 200 from Degussa) | 1 g |
| Ethanol | 5 g |
| Propylene glycol | 5 g |
| Pigments | 5 g |
| Preserving agents qs | |
| Water qs | 100 g |

The mascara applied easily and adhered well to the eyelashes. The film of make-up coated the eyelashes well over their entire length and had good staying power over time. In addition, the mascara was removed with warm water at 35° C.

Example 3

A mascara having the composition below was prepared:

| | |
|---|---|
| Aqueous dispersion of polyether-polyurethane containing 35% solids (Sancure 878 from Goodrich) | 24.5 g AM |
| Hydroxyethyl cellulose (Cellosize QP 4400 H from Amerchol) | 1.82 g |
| Fumed silica (Aerosil 200 from Degussa) | 1 g |
| Ethanol | 5 g |
| Propylene glycol | 5 g |
| Black pigment | 5 g |
| Preserving agents qs | |
| Water qs | 100 g |

The polyether-polyurethane Sancure 878 could be replaced with the polyether-polyurethane Avalure UR-450 or Sancure 861 from Goodrich.

The mascara applied easily to the eyelashes and gave a natural make-up effect with good staying power. After two days, the mascara was removed with warm water at 35° C.

Example 4

A mascara having the composition below was prepared:

| | |
|---|---|
| Aqueous dispersion of polyester-polyurethane containing 49% solids (Avalure UR-425 from Goodrich) | 24.5 g AM |
| Hydroxyethyl cellulose (Cellosize QP 4400 H from Amerchol) | 1.9 g |
| Polytetrafluoroethylene powder (Ceridust 9205F from Hoechst) | 1 g |
| Ethanol | 5 g |
| Propylene glycol | 5 g |
| Pigments | 5 g |
| Preserving agents qs | |
| Water qs | 100 g |

The mascara applied easily and adhered well to the eyelashes. The film of make-up coated the eyelashes well over their entire length and had good staying power over time. The film was also smooth and shiny.

Example 5

A mascara having the composition below was prepared:

| | |
|---|---|
| Aqueous dispersion of polyester-polyurethane containing 49% solids (Avalure UR-425 from Goodrich) | 24.5 g AM |
| Hydroxyethyl cellulose (Cellosize QP 4400 H from Amerchol) | 1.9 g |
| Rice starch | 2 g |
| Ethanol | 5 g |
| Propylene glycol | 5 g |
| Pigments | 5 g |
| Preserving agents qs | |
| Water qs | 100 g |

The mascara applied easily and adhered well to the eyelashes. The film of make-up had good staying power over time and was smooth and shiny. In addition, the mascara was removed with warm water.

Example 6

A mascara having the composition below was prepared:

| | |
|---|---|
| Aqueous dispersion of polyester-polyurethane containing 49% solids (Avalure UR-425 from Goodrich) | 24.5 g AM |
| Hydroxyethyl cellulose (Cellosize QP 4400 H from Amerchol) | 1.9 g |
| Talc (Luzenac 15 M 00 from Luzenac) | 2 g |
| Ethanol | 5 g |
| Propylene glycol | 5 g |
| Pigments | 5 g |
| Preserving agents qs | |
| Water qs | 100 g |

The mascara applied easily and adhered well to the eyelashes. The film of make-up had good staying power over time and was smooth and shiny.

Example 7 Comparative

A mascara not forming part of the invention, having the composition below, was prepared:

| | |
|---|---|
| Aqueous dispersion of styrene/acrylate copolymer containing 45% solids (Neocryl A 1070 from Zeneca) | 27 g AM |
| Hydroxyethyl cellulose (Cellosize QP 4400 H from Amerchol) | 1.82 g |
| Fumed silica (Aerosil 200 from Degussa) | 1 g |
| Ethanol | 5 g |
| Propylene glycol | 5 g |
| Pigments | 5 g |
| Preserving agents qs | |
| Water qs | 100 g |

After applying the composition to the eyelashes, it was found that the staying power of the film of mascara was not as good as that of the film of mascara obtained with the compositions of Examples 1 to 6.

The foregoing written description relates to various embodiments of the present invention. Numerous changes and modifications may be made therein without departing from the spirit and scope of the invention as defined

What is claimed is:

1. A system for coating keratin fibers, the system comprising a reservoir containing a composition for coating keratin fibers and an applicator member for applying the composition to the keratin fibers, wherein said composition comprises an aqueous medium and a film-forming polyurethane in the form of solid particles dispersed in said aqueous medium, wherein said composition has a viscosity, measured at 25° C., at a shear rate of 200 s$^{-1}$, ranging from 5 Pa·s to 18 Pa·s, and wherein said composition is free of wax.

2. A system according to claim 1, wherein said composition is a make-up product for keratin fibers.

3. A system according to claim 1, wherein the applicator member is configured to apply the composition to eyelashes.

4. A system according to claim 1, wherein said polyurethane is chosen from polyester-polyurethanes, polyether-polyurethanes, acrylic-polyurethanes, and siliconed-polyurethanes.

5. A system according to claim 1, wherein said polyurethane is an anionic polyurethane.

6. A system according to claim 1, wherein said polyurethane has a water uptake of less than or equal to 30%.

7. A system according to claim 1, wherein said polyurethane has a water uptake of greater than 30%.

8. A system according to claim 1, wherein said polyurethane is present in an amount ranging from 5% to 60% by weight of solids relative to the total weight of the composition.

9. A system according to claim 8, wherein said polyurethane is present in an amount ranging from 10% to 45% by weight of solids relative to the total weight of the composition.

10. A system according to claim 9, wherein said polyurethane is present in an amount ranging from 15% to 35% by weight of solids relative to the total weight of the composition.

11. A system according to claim 1, wherein said viscosity of said composition ranges from 6 Pa·s to 15 Pa·s.

12. A system according to claim 11, wherein said viscosity of said composition ranges from 7 Pa·s to 12 Pa·s.

13. A system according to claim 1, wherein said composition further comprises at least one thickener.

14. A system according to claim 13, wherein said at least one thickener is chosen from cellulose-based thickeners, guar gums, xanthan gum, carob gum, scleroglucan gum, gellan gum, rhamsan gum, karaya gum, alginates, maltodextrin, starch and its derivatives, hyaluronic acid and its salts, clays, crosslinked polyacrylic acids, polyglyceryl (meth)acrylates, polyvinylpyrrolidone, polyvinyl alcohol, crosslinked acrylamide polymers and copolymers, crosslinked methacryloyloxyethyltrimethyl-ammonium chloride homopolymers, and associative polymers.

15. A system according to claim 1, wherein said composition further comprises at least one ingredient chosen from plasticizers, coalescence agents, fillers, dyestuffs, surfactants, preserving agents, oils and cosmetic agents.

16. A system according to claim 15, wherein said fillers are chosen from fumed silicas, starches, talcs and polytetrafluoroethylene.

17. A system according to claim 15, wherein said fillers are present in an amount ranging from 0.1% to 6% by weight relative to the total weight of the composition.

18. A system according to claim 1, wherein said composition further comprises an auxiliary film-forming polymer.

19. A system according to claim 1, wherein the system further comprises a removable closure configured to close the reservoir.

20. A system according to claim 19, wherein said applicator member is integral with said removable closure means.

21. A system according to claim 1, wherein said applicator member is a mascara brush.

22. A system according to claim 1, wherein said system further comprises a wiper.

23. A mascara system comprising a reservoir containing a composition for coating keratin fibers and an applicator member for applying said composition to the keratin fibers, wherein said composition comprises an aqueous medium and a film-forming polyurethane in the form of solid particles dispersed in said aqueous medium, wherein said composition has a viscosity, measured at 25° C., at a shear rate of 200 s$^{-1}$, ranging from 5 Pa·s to 18 Pa·s, and wherein said composition is free of wax.

24. A system according to claim 23, wherein the system further comprises a removable closure configured to close the reservoir.

25. A process for coating keratin fibers, the process comprising applying a coating composition to the keratin fibers, wherein said coating composition comprises an aqueous medium and a film-forming polyurethane in the form of solid particles dispersed in said aqueous medium, wherein said coating composition has a viscosity, measured at 25° C., at a shear rate of 200 s$^{-1}$, ranging from 5 Pa·s to 18 Pa·s, and wherein said coating composition is free of wax.

26. A process according to claim 25, wherein said process is a make-up process for said keratin fibers.

27. A process according to claim 25, wherein said keratin fibers are eyelashes.

28. A process according to claim 25, wherein the process further comprises applying the coating composition to the keratin fibers with an applicator member.

29. A process according to claim 28, wherein the process further comprises placing the applicator member in a reservoir containing the coating composition to load the coating composition on the applicator member prior to applying said coating composition to said keratin fibers.

30. A process of applying a composition, the process comprising coating keratin fibers with a composition comprising a film-forming polyurethane, wherein said polyurethane is in the form of solid particles dispersed in an aqueous medium, wherein said composition contains no wax and has a viscosity, measured at 25° C., at a shear rate of 200 s$^{-1}$, ranging from 5 Pa·s to 18 Pa·s, and wherein said coat of said composition has at least one property chosen from good staying power on said keratin fibers and capability of being removed with water from said keratin fibers.

31. A process according to claim 30, wherein said coating includes making up said keratin fibers, and wherein said composition is a make-up composition.

32. A process according to claim 30, wherein said keratin fibers are eyelashes.

33. A process of applying a composition, the process comprising coating keratin fibers with a composition comprising a film-forming polyurethane and a filler chosen from starches, talcs and polytetrafluoroethylene, wherein said polyurethane is in the form of solid particles dispersed in an aqueous medium, wherein said composition contains no wax and has a viscosity, measured at 25° C., at a shear rate of 200 s$^{-1}$, ranging from 5 Pa·s to 18 Pa·s, and wherein said coat of said composition has at least one property chosen from good staying power on said keratin fibers, capability of being removed with water from said keratin fibers, and a smooth or shiny appearance on said keratin fibers.

34. A process according to claim 33, wherein said coating includes making up said keratin fibers, and wherein said coat of said composition is a make-up composition.

35. A process according to claim 33, wherein said keratin fibers are eyelashes.

* * * * *